United States Patent
Keown et al.

(10) Patent No.: US 9,478,118 B2
(45) Date of Patent: Oct. 25, 2016

(54) HAND HYGIENE COMPLICANCE CONFIRMATION SYSTEM

(76) Inventors: Sam Keown, Gainesville, FL (US);
Mark Klusty, Gainesville, FL (US);
Eric Laster, Gainesville, FL (US);
Richard Melker, Gainesville, FL (US);
Henry Wohltjen, Gainesville, FL (US);
Ronald Youngblood, Gainesville, FL (US)

( * ) Notice: Subject to any disclaimer, the term of this patent is extended or adjusted under 35 U.S.C. 154(b) by 190 days.

(21) Appl. No.: 14/234,164

(22) PCT Filed: Aug. 17, 2012

(86) PCT No.: PCT/US2012/051245
§ 371 (c)(1),
(2), (4) Date: Sep. 29, 2014

(87) PCT Pub. No.: WO2013/025956
PCT Pub. Date: Feb. 21, 2013

(65) Prior Publication Data
US 2015/0048940 A1    Feb. 19, 2015

Related U.S. Application Data

(60) Provisional application No. 61/524,393, filed on Aug. 17, 2011.

(51) Int. Cl.
*G08B 1/08*  (2006.01)
*G08B 21/24*  (2006.01)
*G06F 19/00*  (2011.01)
*G09B 19/00*  (2006.01)

(52) U.S. Cl.
CPC .......... *G08B 21/245* (2013.01); *G06F 19/327* (2013.01); *G06F 19/366* (2013.01); *G09B 19/0076* (2013.01)

(58) Field of Classification Search
CPC ............... G08B 21/245; G06F 19/327; G06F 19/3493; G06F 19/366; G06Q 10/00; G09B 19/0076
USPC .............. 340/539.12, 573.1, 286.09, 825.54, 340/541, 567, 572.1, 825.06, 505, 603, 540
See application file for complete search history.

(56) References Cited

U.S. PATENT DOCUMENTS

| | | | | |
|---|---|---|---|---|
| 6,727,818 | B1* | 4/2004 | Wildman | G06F 19/3418 340/10.1 |
| 2008/0303658 | A1* | 12/2008 | Melker | G08B 21/245 340/540 |
| 2010/0164728 | A1* | 7/2010 | Plost | G08B 21/245 340/573.1 |
| 2010/0315244 | A1* | 12/2010 | Tokhtuev | G06Q 10/00 340/603 |
| 2011/0057799 | A1* | 3/2011 | Taneff | G06F 19/327 340/573.1 |
| 2011/0169645 | A1* | 7/2011 | Cartner | G06F 19/327 340/573.1 |
| 2011/0193703 | A1* | 8/2011 | Payton | G08B 21/245 340/573.1 |
| 2012/0310664 | A1* | 12/2012 | Long | G06Q 10/06 705/3 |

* cited by examiner

*Primary Examiner* — Daniel Previl

(57) ABSTRACT

Provided according to embodiments of the present invention are Hand Hygiene Compliance Confirmation Systems (HH-CCS) that include a Hand Hygiene Composition Dispenser (HHCD); a Hand Hygiene Composition Dispenser Monitor (HHCDM) and a Hand Hygiene Compliance Monitor (HHCM). In some embodiments, the HHCDM detects when said HHCD dispenses Hand Hygiene Composition (HHC) and signals said HHCM to start a clock so that if the hands of a person are presented to said HHCM within a pre-defined period of time from the time that said HHCDM sends said signal to said HHCM, said HHCM sends a signal to at least one display to indicate hand hygiene compliance, referred to as a Green Light Condition or GLC. Related apparatus and methods are also provided.

15 Claims, 5 Drawing Sheets

$V_C$ : Circuit Voltage
$V_H$ : Heater Voltage
$R_L$ : Load Resistance
$R_H$ : Heater Resistance
$V_{RL}$: Voltage across load resistance

Standard operating conditions:

$V_C$ : 5 V DC
$V_H$ : 0.90 V DC
$R_L$ : Variable ( > 200 Ω)

HAND HYGIENE COMPLIANCE CONFIRMATION SYSTEM

CROSS-REFERENCE TO RELATED APPLICATIONS

This application is the 35 U.S.C. §371 national stage of, and claims priority to and the benefit of, PCT application PCT/US2012/051245, filed Aug. 17, 2012, which claims priority to and the benefit of U.S. Application No. 61/524,393, filed Aug. 17, 2011, the disclosure of each of which is hereby incorporated by reference in its entirety.

FIELD OF THE INVENTION

A Hand Hygiene Compliance Confirmation System (HH-CCS) is disclosed for confirmation of compliance with Hand Hygiene Compliance Procedures (HHCPs) with minimized Response Time (RT) delay.

BACKGROUND OF THE INVENTION

A wide variety of Hand Hygiene Compliance Confirmation Systems (HHCCS) have been described in recent years. Of particular interest to the present invention are the systems disclosed in U.S. Pat. Nos. 7,755,494 and 7,978,083, on the one hand, and of WO2010056534A2 and US2010-0117823 on the other, the disclosure of each of which is herein incorporated by reference. In the '494 and '083 patents, there is disclosed a system whereby the hand hygiene status of personnel (referred to here generally as Health Care Workers, (HCWs), but this is not intended to exclude personnel working in food handling establishments, hospices, old-age homes, and the like—i.e. any personnel working in any facility where hand hygiene monitoring and compliance with hand hygiene protocols is desired come within the ambit of the present invention) is definitively confirmed by detection of volatile compounds on or emanating from the hands of a person who completes a hand hygiene procedure. When hand hygiene procedures have been confirmed, an indicator, for example a light on a Personnel Identification Badge (PIB) (and optionally also on a Hand Hygiene Compliance Monitor (HHCM)) worn by the person is illuminated. Of course, the color of the illuminated light is not critical, but for purposes of ease of description, we shall herein refer to illumination of a light confirming compliance with hand hygiene procedures as a "Green Light Condition", or "GLC".

An embodiment of the HHCCS described in the '494 and '083 patents is included in one embodiment of the WO2010056534A2 and US2010-0117823 system, which, in addition, provides a difference in Time Of Flight (TOF) of sound signals as compared to a electromagnetic signals to confirm the location of a person when completing a hand hygiene procedure, (i.e. on achieving a GLC), and the status of the hand hygiene compliance of a person in relation to any patients in a health care facility, (i.e. does the person have a GLC on approaching a patient in a health care facility).

In relation to the systems and procedures described in the above-discussed patent documents, the present patent disclosure provides an enhancement whereby, from the time a person completes a hand hygiene procedure to the time of achieving a GLC, referred to herein as the Response Time, RT, is optimized so that there is little or no waiting time involved once the hand hygiene procedure is completed to the time that a GLC condition can be achieved. Of course, the system, method and apparatus described herein can be used as a stand-alone system or in combination with a wide variety of existing HHCCSs known in the art, with appropriate modifications which those skilled in the art, based on the present description, are able to make without undue experimentation.

SUMMARY OF THE INVENTION

The system, method and apparatus of this invention, referred to herein as the "fast-to-GLC" system, method and apparatus, provides a means for minimizing the time to achieving a GLC of a person who is required to adhere to a hand hygiene procedure. The fast-to-GLC system can be implemented as an essentially agnostic system in any facility where it is desired to rapidly confirm hand hygiene compliance of people in the facility, or it may be included as an enhancement to the system, method and apparatus disclosed in any or all of the hand hygiene compliance confirmation systems described in U.S. Pat. Nos. 7,755,494, 7,978,083, WO2010056534A2 and US2010-0117823.

The essential components of the fast-to-GLC system, method and apparatus of this invention, in one exemplary embodiment, comprise:
a. a Hand Hygiene Composition Dispenser (HHCD) which contains a Hand Hygiene Composition (HHC), which may or may not contain a detectable marker, and which dispenses the HHC by manual or automatic actuation;
b. a Hand Hygiene Composition Dispenser Monitor (HHCDM) which detects actuation of the HHCD when it dispenses HHC and immediately sends a signal indicating dispensation of HHC; and
c. a Hand Hygiene Compliance Monitor (HHCM) which (i) receives the signal from the HHCDM that HHC has been dispensed, and which, as a result, initiates a routine selected from the group consisting of (1) initiating a sensor, and optionally a fan for drawing in and directing air over the sensor, of a detectable marker on or emanating from the skin of a hand or hands presented to the HHCM, if the HHC contains such a marker, (2) initiating a configurable timer from the time the HHCM receives the signal from the HHCDM that HHC has been dispensed, and (3) a Secondary Confirmation Signal (SCS) generator, selected from the group consisting of a motion detector, an infrared detector, or the like, so that, whether a detectable marker is present in the HHC or not, a SCS is generated to confirm that a hand or hands of a person have been detected by the SCS generator within the time configured into the configurable timer.

While these are the essential elements of the fast-to-GLC system, method and apparatus of this invention, depending on whether this is to operate as a stand-alone HHCCS or is to be included as an enhancement to another HHCCS, additional features, elements and modifications discussed in detail herein below may be included in various embodiments of the invention.

Accordingly, it is a first object of the present invention to provide a system for implementation into a facility where hand hygiene compliance is required which permits confirmation that people within the facility are in fact complying with the facility's Hand Hygiene Compliance Procedures (HHCPs).

Another object of the invention is to provide an enhancement to the systems, methods and apparatuses disclosed in U.S. Pat. Nos. 7,755,494, 7,978,083, and in WO2010056534A2 and US2010-0117823, which minimizes the RT to achieving a GLC following completion of a hand hygiene procedure.

Other objects and advantages of the present invention will be appreciated from a review of the complete disclosure which follows, including the appended claims.

DETAILED DISCLOSURE OF THE PREFERRED EMBODIMENTS ACCORDING TO THIS INVENTION

The present patent disclosure provides a Hand Hygiene Compliance Confirmation System (HHCCS), or an enhancement to an existing HHCCS, for confirmation of compliance with Hand Hygiene Compliance Procedures (HHCPs) established by a facility with minimized Response Time (RT) delay.

In the disclosure which follows, it will be understood where the singular is mentioned (e.g. hand), this should also be taken as applying to the plural (hands) and vice versa, depending on the context. Thus, where a hand is indicated as being presented to a sensor, this could be a single hand or two hands, it generally being understood that if personnel apply Hand Wash Composition to one hand, they are rubbing that hand with the other hand and are not intentionally going out of their way to "game the system" or avoid practicing appropriate hand hygiene procedures. It will also be understood that where the hand(s) of a person is/are referred to, reference may be made to their hand(s), which should be taken to imply his or her hand(s).

In such a HHCCS, with respect to the RT delay, there are at least two objectives which must be met:
A. The first objective is to minimize the RT delay for detection of a detectable volatile marker on or emanating from the hands of a user of the system when such a marker is present in a HHC used in the given facility or a given location in a facility, upon which achieving of a GLC may be predicated. For example, ethanol, isopropanol or the like, present, preferably, in HHCs at a concentration of at least about 10% are disclosed in U.S. Pat. Nos. 7,755,494, 7,978, 083, WO2010056534A2 and US2010-0117823 and can be used for this purpose. HHCs such as waterless alcohol gels which are in common use today in health care facilities and which operate well with the systems, methods and apparatuses disclosed in U.S. Pat. Nos. 7,755,494, 7,978,083, WO2010056534A2 and US2010-0117823 all come within the scope of HHCs for which this objective is relevant.
B. The second objective to accommodate those facilities or those locations in a facility where HHCs are used which do not contain a volatile detectable marker so that a GLC can nonetheless be achieved. This is critically important because not all facilities have implemented soap and water-free HHCs for their HHCPs. In some instances, (i.e. in some facilities or at some locations in a given facility) this is by intention and design, as certain pathogens, e.g. *C. difficile*, and its spores, are not readily killed or inactivated by, for example, alcohol-based, soap and water free HHCs. Thus, this objective of the present invention defines the need for a HHCCS which is agnostic to whether the HHC contains a detectable volatile marker or not, without, at the same time, eliminating the definitive compliance confirmation benefits that can be achieved by detecting volatile detectable marker on the hands of a person. Of course, this objective could be achieved by inclusion of sufficient marker in all HHCs so that, whether soap and water are used or not, the definitive compliance confirmation of detecting the marker on or emanating from the hands of personnel in the facility could be uniformly harnessed. Until such time, however, as all facilities in all locations where HHCCSs are being used also use HHCs which include such markers, the fast-to-GLC method, system and apparatus of this invention provides a critically needed solution.

The essential components of the fast-to-GLC system, method and apparatus of this invention, in one exemplary embodiment, comprise:
  a. a Hand Hygiene Composition Dispenser (HHCD) which contains a Hand Hygiene Composition (HHC), which may or may not contain a detectable marker, and which dispenses the HHC by manual or automatic actuation, the dispensing of HHC from a given HHCD preferably being tracked;
  b. a Hand Hygiene Composition Dispenser Monitor (HHCDM) which detects actuation of the HHCD when it dispenses HHC and immediately sends a signal indicating dispensation of HHC; and
  c. a Hand Hygiene Compliance Monitor (HHCM) which (i) receives the signal from the HHCDM that HHC has been dispensed, and which, as a result, initiates a routine selected from the group consisting of (1) initiating a sensor, and optionally a fan for drawing in and directing air over the sensor, of a detectable marker on or emanating from the skin of a hand or hands presented to the HHCM, if the HHC contains such a marker, (2) initiating a configurable timer from the time the HHCM receives the signal from the HHCDM that HHC has been dispensed, and (3) a Secondary Confirmation Signal (SCS) generator, selected from the group consisting of a motion detector, an infrared detector, or the like, so that, whether a detectable marker is present in the HHC or not, a SCS is generated to confirm that a hand or hands of a person have been detected by the SCS generator within the time configured into the configurable timer.

While these are the essential elements of the fast-to-GLC system, method and apparatus of this invention, depending on whether this is to operate as a stand-alone HHCCS or is to be included as an enhancement to another HHCCS, additional features, elements and modifications discussed in detail herein below may be included in various embodiments of the invention.

In a stand-alone embodiment according to this invention, it will be appreciated that these essential elements require an output, i.e. a GLC condition, to confirm that personnel that have complied with the HHCPs of a given facility have been met. This can be achieved by the simple expedient of the sensor included in the HHCM of element (c) above, once the person who has activated the HHCD presents their (his/her) hand(s) to the HHCM, on detecting the detectable marker on or emanating from the hand(s) presented, sending out a signal (wirelessly, e.g. by infrared, radio frequency, or by any other wireless method known in the art) to a Personnel Identification Badge (PIB) worn by the personnel in the facility, when the PIB of a given person is detected by a Personnel Identification Badge Monitor (PIBM) included as part of the HHCD or located adjacent the HHCD, either as a separate unit or as part of the HHCDM. The signal would, for example, turn on a green (or any other colored indicator) on the PIB, thereby creating a GLC for that person. A similar GLC could also be illuminated at the HHCM itself, to indicate to the person that they have achieved the GLC.

In a variation of this stand-alone embodiment, in addition to confirming detection of the marker, the HHCM could require that the hand(s) be presented to the HHCM within the configured time frame required to generate a SCS. In this embodiment, depending on which is detected first, the GLC could be withheld until the SCS is also achieved once the detectable marker has been detected, or the GLC could be withheld until detection of the marker is also achieved once the SCS has been achieved. Alternatively, or in addition, different degrees of GLC could be defined, e.g. a flashing green light if only the detectable marker is detected or if only the SCS is detected, and a solid green light if both compliance signals are achieved within a configured time frame.

The signal(s) generating the GLC described in these variant embodiments could, of course, also be sent to a central compliance tracking database for the facility, which could thereby track which personnel are compliant and which are not, over an defined period of time.

Where a facility or particular location in a facility does not utilize HHCs which include a detectable marker, the above described embodiment of the fast-to-GLC system would not, of course, generate any signal from the detectable marker sensor. Only the SCS would be generated to confirm that not only has HHC been dispensed to a given person (identified by the PIB worn by the person and the PIBM located in the HHCD or adjacent the HHCD or in the HHCM) from a given HHCD (which dispensing is preferably tracked for each such HHCD), but that person has also presented their (his/her) hand(s) to the HHCM to generate the SCS. Thus, in this embodiment, the SCS "closes the loop", confirming that the HHCDM has not malfunctioned, been disturbed or has otherwise sent off a HHC dispensation signal which is not matched, within a pre-configured time frame, by that person presenting their hand(s) to the HHCM to generate the confirmatory SCS.

In a further embodiment according to this invention, the fast-to-GLC system is utilized in a HHCCS system which also involves a Time of Flight (TOF) element, such as that disclosed in WO2010056534A2 and US2010-0117823. In this embodiment, which operates substantially as outlined above, there is, in addition, the benefit of obtaining granularity with respect to the exact location of a given person who is or is not complying with a facility's established HHCPs by defining the location of personnel in the facility and their status with respect to GLC. Thus, a person wearing a PIB conducting a hand hygiene procedure at a particular HHCD is identified at that particular HHCD by interaction between the PIB and the PIBM as discussed above and then, on achieving a GLC, the person can approach a given patient, for example, and the TOF system would detect that on such approach, that person has a GLC. If they do not have a GLC, a vibration of the PIB or a light at the patient's bed could be illuminated to alert the person that they do not have a GLC and need to engage in a compliant hand hygiene procedure. Optionally, in addition to or in place of a vibrational reminder signal, any other type of reminder signal may be included, such as, but not limited to, an auditory signal, a light signal or the like.

In a further embodiment according to this invention, the system, method and apparatus of the present invention is implemented in a facility which has installed a Hand Hygiene Compliance Confirmation System (HHCCS) according to an embodiment of any one or a combination of U.S. Pat. Nos. 7,755,494, 7,978,083, WO2010056534A2 and US2010-0117823. Such a HHCCS includes the following elements:

1. At least one Hand Hygiene Composition Dispenser (HHCD);
2. At least one Personnel Identification Badge (PIB) worn by at least one Health Care Worker (HCW), which includes a light which is illuminated when hand hygiene compliance is confirmed, that is, the have the desired GLC;
3. At least one Personnel Identification Badge Detector (PIBD) which is part of the HHCDM or is separately located adjacent the HHCD for confirmation of the identity of the HCW on approaching with sufficient proximity, defined by the system, preferably, as being no more than an arm's length from the HHCD; and
4. At least one Hand Hygiene Compliance Monitor (HHCM), located adjacent the HHCD, either as part of the same unit as the PIBD or as a separate unit.

Figure 1:
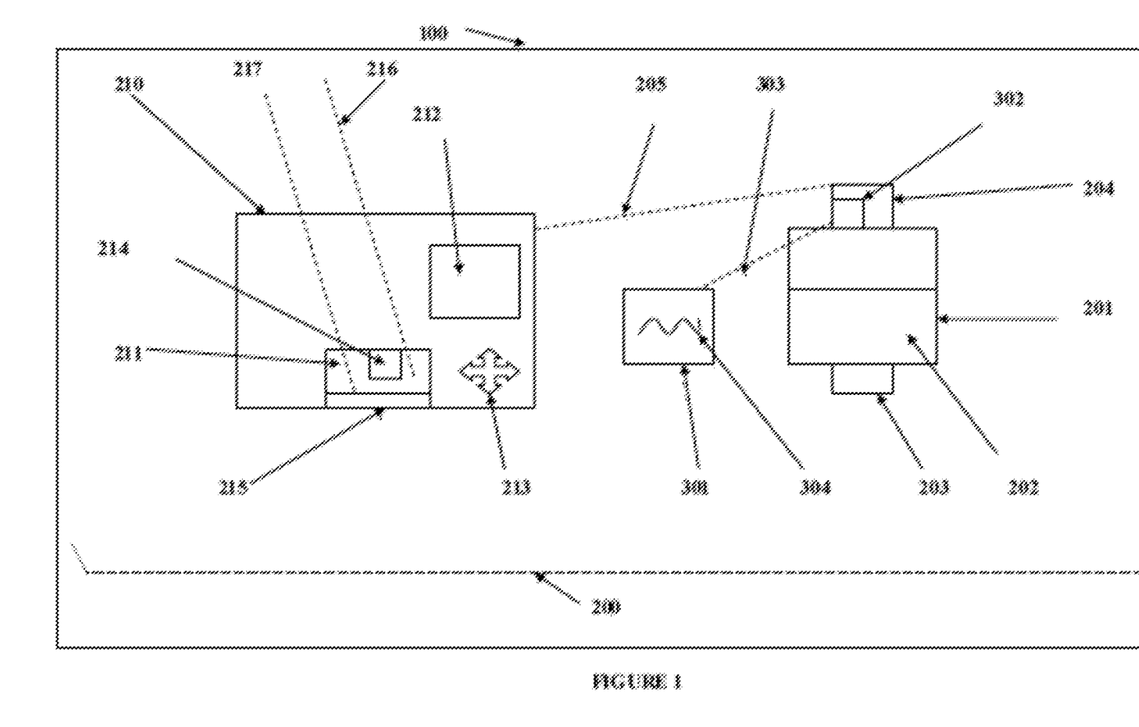
FIG. 1 provides a schematic representation of the various elements of the fast-to-GLC system, apparatus and method of the present invention.
Figure 2:
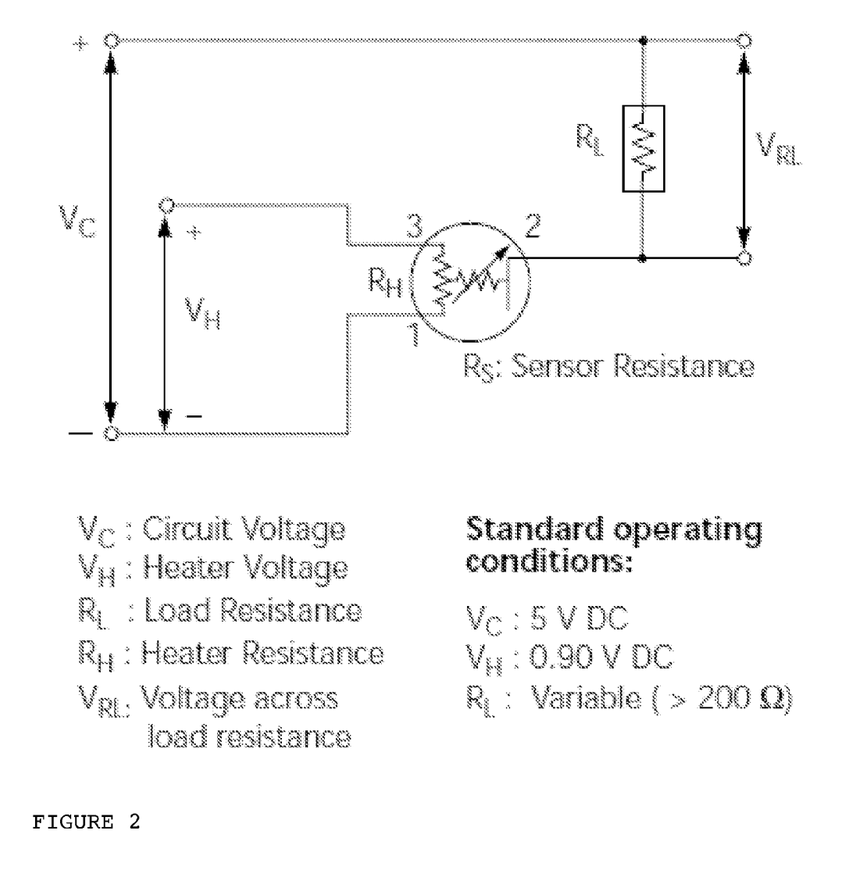
FIG. 2 provides a representation of an SB-30 Operating Model sensor for alcohol, (see FIS Gas Sensor for Alcohol Detection, FIS Inc, www.fisinc.co.jp, May 1999).

To assist in comprehending this invention, reference is now made to FIG. 1, which provides a schematic representation of a facility 100 in which a HHCCS 200 according to this invention is deployed. Included in this system is a Hand Hygiene Composition Dispenser HHCD 201 which contains a Hand Hygiene Composition 202 which is dispensed via actuation means 203. The actuation means may be a manual lever, for example, or it may be an automatic system which, for example, detects when a person places their hands below the HHCD, and an aliquot of HHC is dispensed from the HHCD. A Hand Hygiene Composition Dispenser Monitor HHCDM 204 detects when HHC 292 is dispensed from the HHCD 201 via actuation means 203. When the HHCDM 204 detects actuation of the HHCD 201, it sends a signal 205 to a Hand Hygiene Compliance Monitor HHCM 210. The HHCM 210 includes a Secondary Confirmation Signal SCS generator 211, a sensor 212 (see also FIG. 2 for details) and a fan 213. On receiving the actuation signal 205 from the HHCDM 204, a configurable timer 214 included in the SCS generator 211 initiates a count-down process so that if a hand is detected by a hand detection means 215 included in the HHCM 210 within a configured time, a SCS 216 is generated by the SCS generator 211. In addition, on receipt of the actuation signal 205 from the HHCDM 204 the fan 213 is started and the sensor 212 is initialized (it being appreciated that fan starting and sensor initialization need not occur simultaneously), so that any time required for the fan to come up to speed and draw air over the sensor, and any time delay for the sensor to come to operating temperature, is initiated on actuation of the HHCD rather than upon detection of the hand at the HHCM 210. To confirm the identity of a person actuating the HHCD 201, each person in the facility who is required to adhere to the HHCPs of the facility is issued a Personnel Identification Badge PIB 301 (optionally bearing written information 304 about the person to whom the PIB has been issued) which can be read 303 by a Personnel Identification Badge Monitor PIBM 302 which may be part of the HHCDM 204, or which may be a separate unit or which may be included as a component of the HHCM 210. On confirming detection of a marker by the sensor 212 a signal 217 is generated to confirm positive compliance with the HHCPs of the facility. The signal 217, the signal 216, the identity of the person obtained from the PIB 301, the location or identity of the particular HHCD 201, the time, day and year, etc are all data points which are preferably collected in a central database for monitoring compliance by personnel within the given facility. Of course, the elements of the HHCCS 200 discussed above and shown in FIG. 1 are merely one iteration of the system as implemented in a given location in a facility. Depending on the size and nature of the facility, as many of the HHCDs 201, HHCMs 210, PIBs 301, and other represented and described elements of the system may be provided to ensure convenient coverage and access for all personnel in the facility.

Bearing these features of this embodiment of the fast-to-GLC system of the present invention in mind, the remainder of the description as to how the system operates may be better understood. It will be appreciated, however, that, of course, various elements of the system as shown in this figure and outlined above, need not be configured precisely as outlined here or as shown in the figure. Thus, for example, while the HHCDM 204 is shown above the HHCD 201, it could be mounted on the side of the HHCD 201, or it may be a separate unit altogether, so long as it is still able to detect actuation of the HHCD 201 when HHC 202 is dispensed therefrom. In fact, the HHCDM 204 could be part of the HHCM 210, for example, where actuation of the HHCD 201 is automatic (e.g. on detection of a hand below the dispenser, or upon detection of a PIB 301 by the PIBM 302 when such a PIB is in sufficient proximity to the PIBM to indicate that the person bearing the PIB is close enough to actuate the HHCD.

Similar modifications, permutations and combinations of the various elements described above will occur to those skilled in the art, and, making such a modification does not remove the as-modified system from the scope of the present invention. Thus, another modification that may be contemplated is where, for example, instead of the fan 213 and sensor 212 for detecting volatile marker on or emanating from the hands of a person who has used a HHC 202 which contains such a volatile compound, the HHC 202 may, instead, contain, for example, a fluorescent marker, and in this event, the sensor and fan would be replaced with or supplemented with a light which causes the fluorescent residue on the hands to fluoresce, and a sensor which detects the fluorescence.

In such a system, if the HHCD contains a Hand Hygiene Composition (HHC) containing a sufficiently high concentration of a detectable marker, such as a volatile compound, such as is the case in an ethanol or isopropanol based gel, (typically a water-free composition with greater than 10% volatile compound, and often as high as 65% or more volatile compound such as ethanol or isopropanol or a combination of such agents), then a definitive HHCCS such as that described in U.S. Pat. Nos. '494 and '083 is implemented, with the enhancement of the fast-to-GLC of the present invention. Such a system includes a HHCM which detects the volatile compound on or emanating from the hands of the person after they dispense the HHC from the HHCD onto their hands and present their hands to the HHCM. The Response Time (RT) for an "un-primed" HHCM to detect volatiles on or emanating from the hands of a person who has used such a HHC may be on the order of from about two (2) to about five (5) seconds or more, measured from the time that the hands are presented, thereby delaying the speed with which a GLC on that person's PIB can be achieved. Such delay can occur because of a number of factors. For example, there may be a response time delay in the sensor of the volatile compound in the HHCM because the sensor may need to heat up to operating temperature before it can provide reliable detection of volatile compounds. Alternatively or in addition, there may be a delay in a fan coming up to speed to draw air into the HHCM and across the sensor so that the sensor can detect the volatile compounds. Both of these and other delays may operate together to create a delay in RT which, for example, in a health care facility, may be found to be unacceptably long, given the number of times that health care workers in such facilities have to undertake hand hygiene compliance procedures (before and after each unique patient visit, with many such unique patient visits per day).

The fast-to-GLC system of the present invention may be used in such an implementation of a HHCCS to minimize the delay in RT by essentially priming the sensor and the fan and other components of the system as necessary. This is achieved by the HHCDM immediately sending a signal to such components of the system as necessary to initialize as soon as the HHCDM detects that HHC has been dispensed from a given HHCD. A HHCCS including the fast-to-GLC of the present invention in this scenario includes a HHCD Monitor (HHCDM) which:
(a) monitors the dispensation of HHC from the HHCD;
(b) immediately sends a signal to the HHCM
(i) to initialize the sensor;
(ii) to the fan to initiate the drawing in of air;
(iii) to a hand motion or temperature sensor so that the person can present their hands to the HHCM; and
(iv) to a clock to initiate a count-down-time from the time of detection of the HHC dispensation.

In the time between dispensing of the HHC onto their hands, rubbing the composition on their hands to achieve enhanced hygiene, and then presenting their hands to the HHCM, the HHCM systems will have been initialized and primed so that immediate or almost immediate (about 1 second time frame) detection of volatiles emanating from the hands of the person can be achieved. That is, the delay that could otherwise occur is foreshortened by virtue of the HHCDM sending the above described signals to the HHCM as soon as it detects that HHC has been dispensed from the HHCD.

It should be noted in this context that, in addition to the detection of the dispenser actuator (vibration sensor, infrared sensor or the like) to start the warm up of the alcohol (or other marker) sensor and/or fan operation, the pre-trigger mechanism disclosed herein provides the further advantage that the sensor is operating (on start up) in a marker-free environment. This allows the HHCM sensor in an embodiment for marker detection to perform a baseline measurement of the sensor voltage without marker present. This simplifies the marker detection algorithm. Voltage changes from this baseline measurement are measured and attributed to the marker concentration which is present after the hand is detected as being present below, in front of or within sufficient proximity to the monitoring device to provide reliable measurement of marker on or emanating, in entrained air, from the hand(s) of a user of the system. This feature, in addition, enables the measurement of lower concentrations of marker in the HHC than might otherwise be the case, to operate with multiple Hand Hygiene Compositions of varying marker concentrations in the same location, all the while simplifying the detection algorithm.

In this embodiment of the present invention, the HHCM is able to definitively confirm compliance with required hand hygiene procedures by detection of volatile (or e.g. residues of a fluorescent or otherwise detectable) compound on or emanating from the hands of a person who has been identified (via communication between the PIB worn by the person and the PIBD subsystem, either built into the HHCD, or as a separate unit or included in the HHCM). In addition, the system is able to further confirm compliance when a hand motion or infrared monitor built into the HHCM confirms hand presentation, provided the person presents their hands to the HHCM within a pre-determined time frame from the time that the HHCDM first detects the dispensation of HHC. The pre-determined time frame can be pre-set by the administrator of the system to any desired tolerance and this can be modified in the course of experience as the system is used. Thus, for example, it may be found that, in practice, when a person is using a volatile containing gel, the time from dispensing of the HHC to the time that they present their hands should never be less than about two (2) seconds, and never needs to be more than about ten (10) seconds. As soon as a person presents their hands and motion or heat from the hands is detected within the permitted 2-10 second time frame measured from the time that the HHCDM starts the pre-configured timer, a Secondary Confirmation Signal (SCS) can be initiated by the HHCM which confirms compliance with the required HHCPs. In this instance, of course, there is already the definitive compliance signal achieved on detection of volatile compound on or emanating from the hands of the person whose identity has been determined via the PIB and the PIBD subsystem. Should the volatile compound sensor, for any reason, not be operating or not be operating quickly enough, the person can, in any event, obtain a GLC by presenting their hands within the pre-configured time period from the detection of the HHC dispensation (detected by the HHCDM), and so, the system, method and apparatus of this invention provides what is essentially a fail-safe system so that personnel can achieve a GLC by either definitive detection of the volatile compound on or emanating from their hands, or by timely presentation of their hands from the time that HHC has been dispensed, or both.

Of course, in a given context, the HHCCS of this invention may be configured so that a GLC can only be achieved if the volatile compound sensor and the hand presentation sensor (motion, infrared or other equivalent means) both confirm compliance. Alternatively, the HHCCS may be configured so that a GLC can only be achieved if the volatile compound sensor confirms compliance by detection of the volatile compound, and the Secondary Confirmation Signal (SCS) may be given no weight at all (e.g. in a facility where only alcohol-based hand rubs are permitted). Thus, the system according to this invention provides the facility in which it is implemented with added degrees of flexibility in defining which criteria are adequate to achieve a GLC. The configuration may be standardized across a facility or may be configured differently at particular locations in the facility, as considered prudent by those tasked with establishing the appropriate HHCPs for the facility or given location in the facility.

In a second embodiment according to this invention, all of the same considerations as discussed above apply, with the exception that in this embodiment, the HHC used in the facility or at a particular location in the facility does not contain an adequate amount of volatile compound for the volatile compound detection component of the system to operate or to operate reliably or sufficiently rapidly to meet the requirements of the staff working in the facility. That is, in this embodiment, there is no definitive confirmation of hand hygiene compliance because the HHC in use does not contain a marker, or does not contain the marker in sufficient concentration, to make it possible for the sensor described above to reliably detect the marker (volatile compound or another marker which can be included for the purpose of being detected on the hands of people who are compliant in the hand hygiene procedures specified by the given facility). HHCs such as soap, still used in many food handling and health care and old age care facilities, hospices and the like, may well contain insufficiently high levels of volatile compound to be detected by the sensor described above in the first embodiment of this invention. In that case, the Secondary Confirmation Signal (SCS), i.e. the detection of hand motion or hand heat at the HHCM, acts as the primary confirmation signal for confirming hand hygiene compliance. Thus, so long as the person activating HHCD presents their hands to the HHCM within the pre-defined time period from the time that the HHCDM starts the timer, based on its detection of HHC being dispensed from the HHCD, that person can still secure a GLC for the hand hygiene procedure.

It will be appreciated by those skilled in the art that in a given scenario, the Response Time (RT) of the system can be such that Health Care Workers (HCW's) (old-age caregivers, food handlers, etc.) can obtain a Green Light Condition (GLC) on their identification badges (PIBs) (and, optionally, also illumination of a GLC at the HHCM), within a time frame of less than about one (1) second when alcohol is not intended to be sensed and within about one (1) to about two (2) seconds when alcohol or another marker is intended to be detected as definitive confirmation of compliance with the HHCPs. Of course, it will be appreciated by those skilled in the art that another marker than a volatile compound could be included in the HHC for this purpose—e.g. a marker could be included in the HHC which leaves a residue on the hands for a limited amount of time following a hand hygiene procedure which can be detected on the hands of the person. Thus, for example, a fluorescent residue could be detected, and in such an implementation of the HHCCS of this invention, the sensor would not be a volatile marker sensor but would, instead, be a light which causes the marker to fluoresce, and that fluorescence would to be detected for definitive compliance. In any event, on completion of a hand hygiene procedure, the person presents their hand(s) to the HHCM within a time period initiated by the HHCDM. In time, the acceptable time-frame tolerances may be refined by the administrators of the system, but the solution being implemented would preferably be capable of performing at the extremes, i.e. as measured from the time that the HHC is dispensed from the HHCD (as detected by the HHCDM), a time period of about 3 seconds at the low end of the time period to about 15 seconds at the high end of the time period, should provide sufficient flexibility for almost any facility in which the HHCCS of this invention is implemented. The tolerances could be set and refined as the empirical data/feedback from HCW's is obtained in the field. Preferably, the RT is agnostic with respect to whether the HHC being used is an alcohol based composition or a soap based composition.

The fast-to-GLC apparatus of this invention preferably comprises a HHCDM which can detect dispensing of HHCs from any of a number of different HHCDs in common use. Thus, in one embodiment according to this invention, the HHCDM comprises, for example, a micro-machined accelerometer (of which there are many known in the art and which are commercially available, including but not limited to, for example, those available from Analog Devices, e.g. the ADXL 335, a vibration sensor (e.g. a Signalquest P/N SQ-SEN-200) and the like) which is affixed to an existing HHC dispenser in a hospital, hospice, old age home, food handling facility or any other location where monitoring of compliance with hand hygiene procedures is desired. The accelerometer detects vibrations caused on actuation of the HHCD and, immediately upon detection of such vibrations initiates a routine as described below. Alternatively, the HHCDM may comprise a relay from an automatically actuated HHCD and/or it may comprise a hand motion or infrared monitor which detects presentation of the hand(s) to the HHCD. In such embodiments, or as a separate actuation means, the approach of a person within the facility to a sufficiently close proximity to the HHCD to permit communication between the PIB worn by the person and the PIDM at the HHCD (included in the HHCD, as a separate unit, included as part of the HHCDM, or as part of the HHCM), permits dispensation of HHC onto the hand(s) of the person upon detection, for example, of the motion of hands or heat of the hands below the HHCD. Automated HHCD systems such as this are well known and commercially available and are therefore not described in further detail here. The critical element for the present invention being, however, that the automated dispensing or manually actuated dispensing of the HHC is coupled with a signal, i.e. as part of a HHCDM, which initiates a routine which:

a. initiates the marker detection system—for a detectable volatile marker, a fan is initiated to draw in air with entrained detectable volatile compound (e.g. alcohol or other volatile marker) in the HHC emanating from the HCW's hands; warming of a metal oxide sensor (MOS) or other appropriate sensor, is initiated so that it comes to operating temperature to detect the alcohol (or other marker); in this manner, the response time for alcohol-based compositions to achieve a GLC once a hand is detected under the HHDM is limited to between about 1-2 seconds. Note: if the system allows from 3-10 seconds for the HCW to present their hand(s) to the HHCM for detection by IR or motion sensing, that detection could illuminate a blinking light on the PIB, and, up to an additional 2 second may be permitted for the light to become e.g. a solidly illuminated green light on detection of the marker. Alternatively, the routine could be such that the light is solidly illuminated, whether the marker is detected or not; and b. for alcohol-free HHCs, if the HCW presents their hand(s) to the HHCM and a motion/IR sensor in the HHCM detects the hand(s) within a limited time frame of about 3-10 seconds from receipt of the HHCDM's HHC dispensation detection signal (e.g. vibrations caused on actuation of the dispenser), then the HCW can likewise achieve a GLC.

It will be appreciated by those skilled in the art that other HHCD actuation detection means, other than use of an accelerometer, may be employed and achieve similar results and benefits for the reduction in RT. Thus, for example, a level sensor, a pressure sensor, or a weight sensor for the HHC, on detecting a change in the amount of HHC, or a hand motion or infrared sensor can initiate similar or identical routines to those outlined above for the accelerometer containing or other embodiments of the fast-to-GLC system of this invention. Likewise, for example, a video monitoring system could actuate similar routines on detection of an individual actuating release of HHC. Alternatively, or in addition, on detection by a PIBM of a PIB within sufficient proximity to the HHCD, a set of routines as described above is initiated to similarly minimize any delay in RT. An infrared detector or motion detector at the HHCD which detects that a hand has been presented for receiving HHC, can serve as the HHCDM, or, upon detection of hand presentation by such a detector, a PIBM can be activated to confirm detection of a PIB within sufficient proximity to record a HHCD actuation. In a preferred embodiment according to this invention, the HHCDM includes the accelerometer as described above, alone or in combination with any other HHC dispensation detection means.

EXAMPLES

While the foregoing description generally describes and enables the fast-to-GLC HHCCS of the present invention, and how it can be integrated into use in an existing HHCCS, the following examples are provided to ensure that those skilled in the art are enabled to practice this invention without undue experimentation, to disclose the best mode of practicing this invention as contemplated by the present inventors at the time of filing of this application, and to ensure a thorough and complete written description of the invention. It will be appreciated, however, that the specifics of the examples provided here are not limiting on the invention, and, for example, elements described in one example may be combined with elements described in another example. Rather, for an appreciation of the scope of the invention, the entire disclosure should be considered, including the claims as appended and equivalents thereof.

Example 1

HHCCS without Requiring Detection of HHC Marker

A HCW in a health care facility activates a particular HHCD in the facility, causing an accelerometer included in a HHCDM affixed to the HHCD to detect that the HHCD has dispensed HHC.

The HHCDM sends a signal to a PIBM to initiate communication with a PIB to confirm that a HCW can be identified at the particular HHCD. RFID and similar communication protocols for such communication between PIBs and PIBMs are well known in the art. Upon detection of a "ping", a signal is sent to the HHCM starting a timer permitting from 3-15 seconds, measured from the time of detection of the HHC dispensation, for the HCW to present their hand(s) to the HHCM. If this is done within the permitted 3-15 seconds time frame, a signal is sent from the HHCM to the badge to cause an LED included in the PIB to blink "green". A similar LED included in the HHCM blinks "green", and a partial GLC will have been achieved.

Example 2

A Complete Cycle for Soap where Detection of a Volatile, Such as Alcohol, is not Possible 1. HCW activates a HHCD, causing an accelerometer in the HHCDM to detect dispensing of HHC;
2. The accelerometer activates a fan and MOS sensor in the HHCM if the HHCM is positioned where either a soap product or an ethanol containing gel or foam dispenser is co-located.
3. If the HHCM is positioned where only a soap product is present, then the fan and MOS sensors are not activated, or, if activated, their function is not relevant to the HCW achieving a GLC at that location.
4. If the HCW's PIB and a PIBM included in the HHCM located at that HHCD complete communication any time up to 10 seconds, (and preferably within about 5 seconds), after detection of the HHCD activation, a "Level One" hand wash event is recorded and the green light on the PIB is set to blink.

5. If the HHCM detects presence of the HCW's hand(s) within about 5-10 seconds after activation of the HHCD, a "Level Two" hand wash event is recorded and the green light on the PIB stays illuminated.

6. For products not containing or containing insufficient alcohol either of these two events (Level One or Level Two detection) is set by the administrators of the facility's HHCCS to be sufficient to record a successful hand hygiene event.

Example 3

A Complete Cycle for an Ethanol Containing Gel or Foam (>60% Ethanol)

A HCW activates HHCD causing an accelerometer included in a HHCDM to detect dispensing of HHC. The HHCDM sends a signal to the HHCM to activate a fan and MOS sensor in the HHCM if the HHCM is positioned where either a soap product or an ethanol containing gel or foam dispenser is co-located or only ethanol containing products are located. If the HCW's PIB and a PIBM included in the HHCM complete communication any time between about 5-10 seconds after the HHCDM detects HHCD activation, a "Level One" hand wash event is recorded and the green light on the HHCM and PIB flash green. If the HHCM detects presence of the HCW's hand(s) at any time between about 5-10 seconds after activation of the HHCD is detected by the HHCDM, a "Level Two" hand wash event is recorded and the green light on the HHCM and PIB stays illuminated. If the HHCM detects presence of ethanol a "Level Three" hand wash event is recorded. It should be noted that a GLC always occurs within seconds of detection of a hand under the HHCM, whether alcohol is detected or not, provided the hand(s) of the HCW are presented to the HHCM within the allotted time-frame from the detection of actuation of the HHCD. In a refinement of this system, once the hand is detected under the HHCM, the green light on the HHCM and on the PIB blinks green, and upon detection of alcohol or other marker on or emanating from the hand(s) of the HCW, or on reaching a maximum of 2 seconds from the time of detection of the hand(s) (by motion, heat, video or equivalent means), the light on the HHCM and PIB remains solidly illuminated.

Example 4

Probablisitic Approach to Documentation of Hand Hygiene Compliance

In this embodiment of the fast-to-GLC HHCCS, three levels of validation of hand hygiene compliance may be provided for, see Table 1 below:

TABLE 1

| Verification Levels for Hand Hygien | Dispenser Actuation | Hand Motion Within Configured Time | HHC: Non-Alcohol | HHC: Alcohol or Other Marker |
|---|---|---|---|---|
| Level - I | X | | X | |
| Level - II | X | X | X | |
| Level - III | X | X | | X |
| Level - IV | X | | | X |

In such an implementation of this invention, a probabilistic model becomes available to ensure that HCWs are actually practicing good hand hygiene procedures. For instance, at HHCMs located adjacent to soap dispensers, it will only be possible to detect Level I or Level II events.

Level I events are considered to represent "possible hand hygiene compliance events", while Level II events are considered to be "probable hand hygiene compliance events", since the hands are actually detected under at the HHCM within the configured time frame. The value of Level I events lies in the fact that the HHCCS of this invention, as a stand-alone system or as an enhancement to an existing HHCCS is still capable of distinguishing, based on the PIB-PIBM communication protocol, the only HCW who could be responsible for actuating the HHCD at a given location, even if several HCWs are in the vicinity. This is particularly the case where the fast-to-GLC system of this invention is included as an enhancement to HHCCS in which the location of a given HCW is either tracked or can be confirmed via, for example, difference in time of flight (TOF) signals in communication with the PIB of all of the HCWs in the facility.

Level II events, of course, include the added confirmation that the identified HCW further confirms their compliance by presenting their hand(s) to the HHCM within the configured time frame as measured from the time that the HHC has been dispensed. This eliminates the possibility of a false compliance event being recorded for a given HCW because they were identified at a given HHCD when a HHCDM signal is generated to show that HHC has been dispensed from that HHCD.

Level III events can only be detected at HHCMs positioned adjacent HHCDs which dispense HHCs containing alcohol or another marker which can be definitively detected on or emanating from the hands of the HCWs in the facility. When alcohol is detected, for example, under Level III, this is treated as a "documented hand hygiene event", provided there are no missing elements in the chain of the event—e.g. a missing HHCDM signal indicating actuation of the HHCD.

A Level IV event is one where there is a documented HHCD event and positive identification of marker on or emanating from the hand(s).

In light of the different levels of hand hygiene compliance accommodated by the fast-to-GLC system, method and apparatus of this invention, further granularity can be obtained, based on knowledge of where the HCW interacted with a HHCD, whether alcohol is even present in the HHC at that HHCD, and what the likelihood of a detection within 1 second of alcohol being dispensed is when the fan is activated and the MOS heated before the hand is detected under the HHCM. For instance, if the best possible rate of alcohol detection is 75%, then HCWs who activate HHCDs which contain alcohol and have a 70% ethanol detection rate are probably compulsive about their compliance with the HHCPs of the facility. By contrast, for example, a HCW with only 20% ethanol detection is probably "gaming the system" by persistently and intentionally not allowing sufficient time for ethanol to be detected. Of course, knowledge of the percentage of time that a HCW uses soap as opposed to alcohol containing products is important, since this could dramatically affect the rate of alcohol detection. This may occur in a room where a patient has a documented *C. difficile* infection, which requires the use of soap and water to remove spores.

It is preferred for the GLC of each person in the facility subject to complying with the facility's HHCPs to be stored in a database. This is achieved by methods, means, systems and apparatuses well known in the art.

For example, the HHCM on confirming the identity of a person via the PIBM sends, via a wired or wireless communication means, both the identity of the person and their GLC for any hand hygiene procedure conducted at that HHCM. This data can be stored in a central database and can be analysed for hand hygiene compliance trends across the facility, for a given individual and for all personnel in the facility who are required to adhere with the facility's HHCPs. Over time, this stored data is analyzed and remedial action can be taken to ensure compliance if any personnel are identified to be consistently or sporadically non-compliant. In addition, by tracking GLC of various personnel in the facility, it is also possible for the system to assist in tracking any infections that are spread inside the facility by correlating when and where such infections occur and comparing that data with the data in the database relating to which individuals have or have not complied with the HHCPs of the facility. By careful analysis, such data can reveal how and possibly even who may be responsible for carrying infectious agents, fomites and the like from one location in the facility to another.

Example 5

Figure 3:
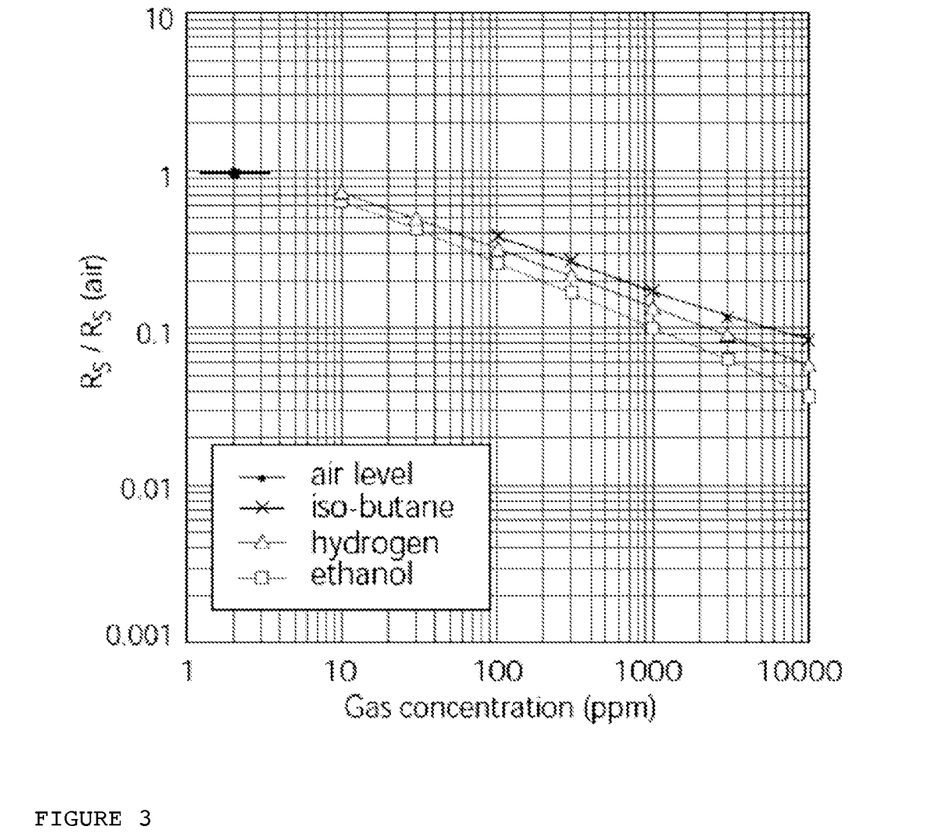
FIG. 3 shows sensitivity characteristics of the sensor represented in FIG. 2.

Application of the Fast-To-Green HHCCS of this Invention in the Context of a Commercially Available HHCCS, the Hygreen™ System I. Background In a commercial HHCCS known as HyGreen™, there is included a FIS SB-30 Gas Sensor. The SB-30 is a tin dioxide semiconductor gas sensor with a high sensitivity to alcohol. A representation of the operating model for such a sensor is provided in FIG. 2. The change in sensor resistance (Rs) is obtained as the change in output voltage across a load resistor. The sensor resistance decreases with an increase of gas concentration based on a logarithmic function, see FIG. 3.

Field operation determined that the sensor can drift over time and with use. Absent the application of the present inventive solution, this could result in intermittent results when identifying the presence of a marker, such as alcohol.

II. Run Characterization

Figure 4:
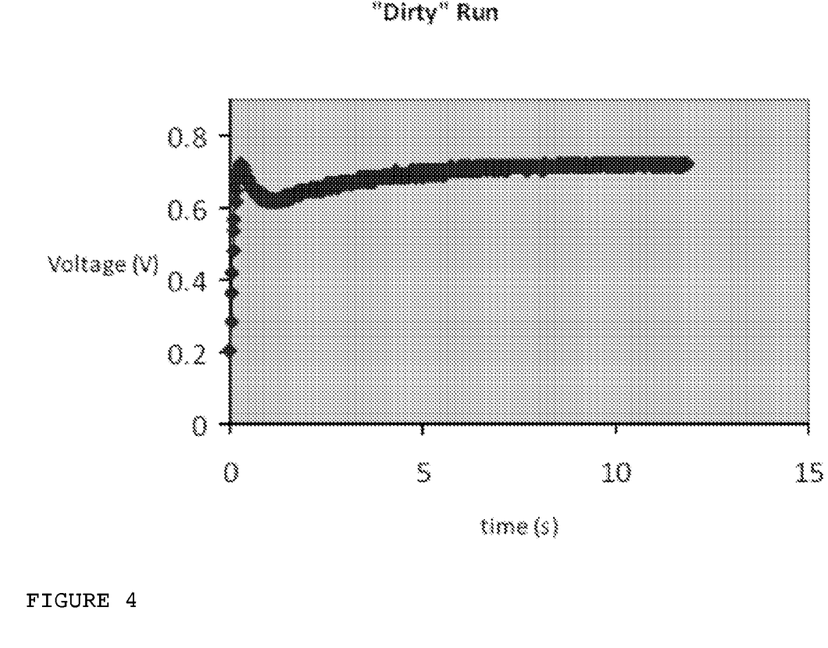
FIG. 4 shows an tracing of the output signal from the sensor of FIG. 2 when no alcohol is present.

Using LabView and a Measurement Computing DAQ module the signal measurement from the sensor circuit was observed during air and alcohol exposure. Typically a cycle with no alcohol will produce a signal noticeably greater than a cycle with alcohol present. FIG. 4 depicts what a typical run looks like when no alcohol has been exposed to the sensor. As can be seen, a transient artifact can occur from time zero to approximately the four second mark. Normally the sensor is off to conserve power; this artifact is a result of the sensor being switched on and warming. Also, remnant alcohol particles can contribute to this effect. This transient phenomenon has been observed lasting as long as 5 seconds, depending on the particular sensor that is selected for observation.

Figure 5:
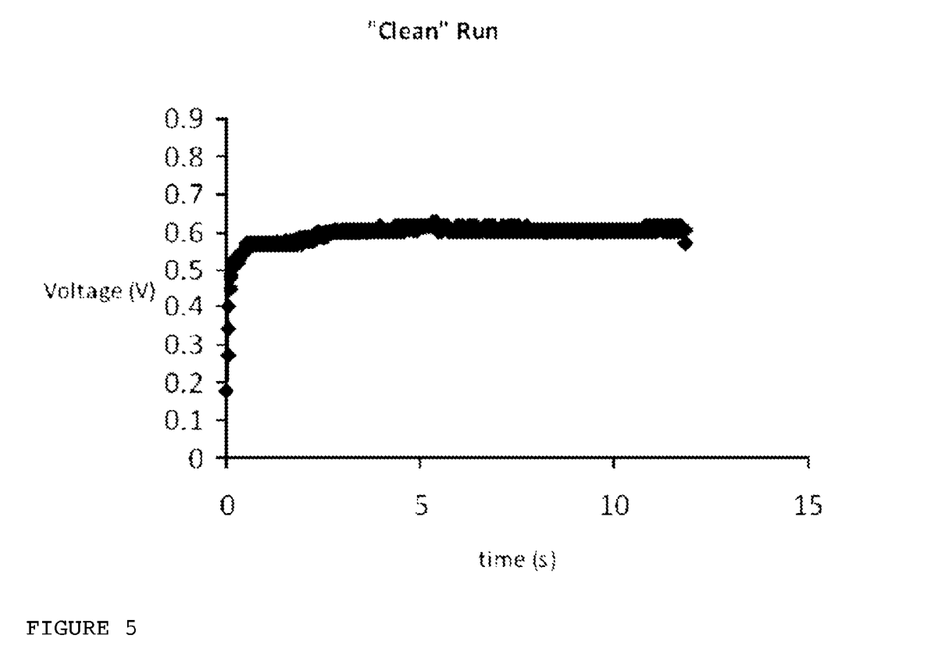
FIG. 5 shows a tracing of the output signal from the sensor of FIG. 2 when alcohol is present.

FIG. 5 depicts the output of a "normal" cycle when alcohol is present, but the system of the present invention is not included in the commercial embodiment of the HyGreen™ HHCCS. On implementation of the system of this invention, clean signal is achieved at all times, so long as adequate time is permitted for an ambient air signal to be taken to zero-out the baseline of the sensor in the absence of detectable marker. This would be Level 4 and Level 3 up until the system times out and provides a green compliance signal.

Signal on Implementation of the Dispenser Hand Wash Sensor of this Invention

Through visual inspection it is observed that, at steady state, there is nearly 100 mv of signal difference between the hand wash interaction with no alcohol present and the hand wash interaction with it present. However the requirement for a fast response allows the transient artifact could influence the process because the signal during this period can be as small as a typical run with alcohol present. These factors, along with potential for the output of the sensor baseline to drift can contribute to false positives and slow time-to-green (i.e. definitive detection of marker on or emanating from the hand(s) of a person utilizing the system).

III. Dispenser Activated Pre-Triggering of HHCM

1. Warm-Up

Warming the sensor from the time the user engages the dispenser allows for extra time to warm the sensor, reducing the influence of any transient artefact such as that shown in FIG. 4. The timing for this warm-up phase is around 2.5 s. Historic data acquired from a commercial implementation of the HyGreen™ HHCCS indicates that providing a pre-trigger warm-up period of 2.5 seconds should be sufficient for approximately 95% of sensors in use to avoid artifactual interference from the warm up phase. Sensors which have a longer warm-up period or which reveal artifactual interference for a longer period of time can be identified and discarded during the manufacturing process. As will be appreciated, an even faster warm-up time than 2.5 s could be implemented, if needed, but more sensors would need to be eliminated to achieve a consistent set with acceptably fast warm-up response times to avoid artifactual interference.

2. Algorithm

The fast-to-GLC system utilizes an algorithm as follows: Immediately after the warm-up stage and before the user interacts with a HHCD or other components of the system, a room air baseline is taken. Since the baseline is taken when no volatile marker, such as alcohol, is present, any discernibly small difference from this baseline (based on the limits of detection of the given sensor) can be utilized as indicating that marker, such as alcohol, is present. This substantially expands the range of HHCs that can be utilized for definitive compliance in hand hygiene procedures. For example, a soap with low level of volatile organic compound which could not be utilized with a system that includes a sensor with a drifting baseline, or an early warm-up artefact, can now be utilized reliably with the HHCCS provided the fast-to-GLC system of this invention is implemented. The only requirement for reliable function that users not engage the sensor during the warm-up following interaction with the dispenser (HHCD).

IV. Results and Conclusions

Initial testing indicates that the HHCD-activated HHCM rejects a higher percentage of false negatives and false positives (less that one percent) than does a HHCCS in the absence of the implemented fast-to-GLC invention. In addition, units with the fast-to-GLC system implemented provide a reduced response time, such that time-to-green on hand presentation following HHC dispensing and the presentation to the HHCM ranges from less than a second to 1.5 s, depending on the alcohol content present in the HHC (e.g. soap or alcohol-based hand rub) in use. Results of actual testing are shown in Table 2 below, with observed time-to-green of is with sanitizer and about 1.5 s with soap. Equipment utilized for the data shown in Table 1 is a commercial HyGreen™ system with units marked as Test 1-5. One good, working PIB was utilized for communication with a PIBM included in the HyGreen™ system. The procedure involved testing (1) signal pre-warm-up on each machine (Dirty), (2) followed by waiting for 10 seconds, (3) use of soap on and hand presentation to each machine (Soap), (4) followed by waiting for 10 seconds, and (5) sanitizer (alcohol >65%) on and hand presentation to each machine (Sanitizer), (6) followed by waiting for 10 seconds, and, (7) repeating steps 1-6 twenty five times. Where soap was used, it was Deb Med DMAMDF1L, and where sanitizer was used, it was Purell 2156. In the table, V indicates a Pass while an X indicates a failure (there were none). The tests were done in a controlled environment. This kind of performance is what we expect when the sensor is given adequate time to warm and the user is well trained. The time to green in the test wasn't measured in every case and wasn't part of the criteria of success. The initial purpose of the test was to identify that this system would reduce False Positives and False Negatives. If the expected results were observed then the test was defined as a success. It was a given that if the interaction was performed correctly the transaction from the time the hand was presented to green would be faster than without implementation of the system and algorithm described herein.

TABLE 2

| | Unit 1 | Unit 2 | Unit 3 | Unit 4 | Unit 5 | Set Number |
|---|---|---|---|---|---|---|
| Dirty | ✓ | ✓ | ✓ | ✓ | ✓ | 1 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 2 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 3 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 4 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 5 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 6 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 7 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 8 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 9 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 10 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 11 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 12 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 13 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 14 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 15 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 16 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 17 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 18 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 19 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 20 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 21 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 22 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 23 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 24 |
| Soap | ✓ | ✓ | ✓ | ✓ | ✓ | |
| Sanitizer | ✓ | ✓ | ✓ | ✓ | ✓ | |
| Dirty | ✓ | ✓ | ✓ | ✓ | ✓ | 25 |
| Soap | ✓ | ✓ | ✓ | ✓ | ✓ | |
| Sanitizer | ✓ | ✓ | ✓ | ✓ | ✓ | |

What is claimed is:

1. A Hand Hygiene Compliance Confirmation System (HHCCS) comprising:
   a. a Hand Hygiene Composition Dispenser (HHCD);
   b. a Hand Hygiene Composition Dispenser Monitor (HHCDM); and
   c. a Hand Hygiene Compliance Monitor (HHCM);
   wherein said HHCDM detects when said HHCD dispenses Hand Hygiene Composition (HHC) and signals said HHCM to start a clock so that if at least one hand of a person is presented to said HHCM within a pre-defined period of time from the time that said HHCDM sends said signal to said HHCM, said HHCM sends a signal to at least one display to indicate hand hygiene compliance;
   wherein said HHCCS initiates a routine selected from at least one of the following:
   initiating a sensor, and optionally a fan for drawing in and directing air over the sensor, of a detectable marker on or emanating from the skin of the at least one hand presented to the HHCM, if the hand hygiene composition (HHC) contains such a marker;
   initiating a configurable timer from the time the HHCM receives the signal from the HHCDM that HHC has been dispensed; and
   generating a confirmation signal if the at least one hand of the person has been detected by a confirmation signal generator within the time configured into the configurable timer.

2. The HHCCS according to claim 1 wherein said system further comprises a Personnel Identification Badge Monitor (PIBM) which confirms the identity of a person carrying a Personnel Identification Badge (PIB) upon reaching a predefined proximity to said HHCD.

3. The HHCCS according to claim 1 wherein
a confirmation signal is generated and the confirmation signal generator is selected from the group consisting of a motion detector and an infrared detector.

4. The HHCCS according to claim 1 which includes a time of flight (TOF) system for determining the location of any person in a facility in which said HHCCS is deployed.

5. The HHCCS according to claim 4 in which the hand hygiene compliance of any person in a facility in which said HHCCS is deployed is stored in a database.

6. The HHCCS according to claim 1 which is configured to provide a plurality of levels of verification of hand hygiene compliance.

7. The HHCCS according to claim 6 wherein said plurality of levels of verification of hand hygiene compliance comprise:
   i. a second level (Level II) which comprises verification of HHCD actuation and detection of the at least one hand presented for such level of verification within a configured time frame from the time of detection of actuation of the HHCD;
   ii. a third level (Level III) which comprises verification of HHCD actuation and detection of the at least one hand presented for such level of verification within a configured time frame from the time of detection of actuation of the HHCD, and detection of a marker included in the HHC on or emanating from the at least one hand presented for verification in the second level; and
   iii. a fourth level (Level IV) which comprises verification of HHCD actuation and detection of a marker included in the HHC on or emanating from the at least one hand.

8. The HHCCS according to claim 7 which, in addition to any of said plurality of compliance levels, also is configured to provide compliance at a first level, (Level I), requiring only verification of HHCD actuation.

9. The HHCCS according to claim 8 wherein Level I events are credited as representing impossible hand hygiene compliance events, Level II events are credited as representing improbable hand hygiene compliance events, and Level III events are credited as representing undocumented hand hygiene compliance events, provided there are no missing elements in the chain of the event for a given Level event to be confirmed.

10. The HHCCS according to claim 1, wherein
for HHCMs located adjacent to soap dispensers, only Level I or Level II events are detected, and Level III events are only detected at HHCMs positioned adjacent HHCDs which dispense HHCs containing a marker which can be definitively detected on or emanating from the at least one hand presented to the HHCM.

11. The HHCCS according to claim 1 wherein when said HHCDM detects that said HHCD dispenses Hand Hygiene Composition (HHC), said HHCCS confirms hygiene compliance of a person via communication between a PIBM and a PIB carried by the person when they are the only person close enough to activate said HHCD.

12. The HHCCS according to claim 11 wherein said PIBM, on detecting said person and communicating with said person's PIB, sends a signal, via a wired or wireless communication means, both the identity of the person and their hand hygiene compliance for any hand hygiene procedure conducted at that HHCM, said signal being received and stored as data in at least one central database.

13. The HHCCS according to claim 12 which, over time, analyzes said stored data for a facility in which said system is implemented to determine at least one of:
   a. remedial action that could be taken to ensure compliance if any personnel are identified to be consistently or sporadically non-compliant;
   b. the GLC status of personnel in the facility; and
   c. correlations between where and when any infections are spread inside the facility and individuals who have or have not complied with Hand Hygiene Compliance Procedures (HHCPs) of the facility.

14. The HHCCS according to claim 1 wherein said sensor, on receiving said signal from said HHCDM, takes a reading of ambient air prior to hand presentation to establish a baseline sensor signal reading.

15. A method for confirming hand hygiene compliance in a facility which requires hand hygiene compliance comprising:
   deploying in said facility at least one HHCD containing HHC for dispensing onto the hands of personnel in said facility;
   operatively engaging at least one HHCDM which detects dispensing of HHC from said HHCD and which generates a signal on detecting such dispensing;
   operatively deploying least one HHCM so as to receive said signal from said HHCDM and, in response to receipt of the signal, initiates a count-down timer for detection of at least one of the following: a detectable marker or a hand presentation
   wherein the method further comprises at least one of the following routines:
   initiating a sensor, and optionally a fan for drawing in and directing air over the sensor, of a detectable marker on or emanating from the skin of the at least one hand presented to the HHCM, if the hand hygiene composition (HHC) contains such a marker;
   initiating a configurable timer from the time the HHCM receives the signal from the HHCDM that HHC has been dispensed; and
   generating a confirmation signal if the at least one hand of the person has been detected by a confirmation signal generator within the time configured into the configurable timer.

* * * * *